United States Patent [19]

Sherwin et al.

[11] 4,158,100

[45] Jun. 12, 1979

[54] PROCESS FOR THE PREPARATION OF β-PHENYLETHYL ALCOHOL VIA HOMOLOGATION

[75] Inventors: Martin B. Sherwin, Wayne; Arthur M. Brownstein, Wyckoff, both of N.J.

[73] Assignee: Chem Systems, Inc., New York, N.Y.

[21] Appl. No.: 850,209

[22] Filed: Nov. 10, 1977

[51] Int. Cl.$^2$ .............................................. C07C 29/00
[52] U.S. Cl. .................................................. 568/715
[58] Field of Search ......................................... 568/715

[56] References Cited

U.S. PATENT DOCUMENTS

| | | | |
|---|---|---|---|
| 1,315,619 | 9/1919 | Altwegg | 568/715 |
| 1,591,125 | 7/1926 | Harlow et al. | 568/715 |
| 2,726,251 | 12/1955 | Dickey et al. | 568/715 |
| 3,239,566 | 3/1966 | Slaugh et al. | 568/75 |
| 3,285,948 | 11/1966 | Butter | 568/902 |
| 3,479,412 | 11/1969 | Pregaglia et al. | 568/715 |
| 3,514,493 | 5/1970 | Pregaglia et al. | 568/715 |
| 3,867,430 | 2/1975 | Grozhan et al. | 568/715 |
| 3,954,888 | 5/1976 | Baudorn | 568/715 |

FOREIGN PATENT DOCUMENTS 951906 3/1964 United Kingdom.
979908 1/1965 United Kingdom.

OTHER PUBLICATIONS

"J.A.C.S.", vol. 71, pp. 4160-4161, (1949).
Orchim, "Advances in Catalyns", vol.. V, pp. 385-415.
Kryukov et al., "Neftekhimiya", 1970, 10(1), pp. 83-87.

*Primary Examiner*—Norman Morgenstern
*Attorney, Agent, or Firm*—Bert J. Lewen

[57] ABSTRACT

β-Phenylethyl alcohol is prepared by the homologation of benzyl alcohol with hydrogen and carbon monoxide in the presence of a cobalt catalyst promoted with ruthenium and iodine compounds, in the presence of water at a temperature from 100° to 165° C. High yields and selectivity of the β-phenylethyl alcohol are obtained.

6 Claims, No Drawings

PROCESS FOR THE PREPARATION OF β-PHENYLETHYL ALCOHOL VIA HOMOLOGATION

BACKGROUND OF THE INVENTION

It has long been desirable to prepare β-phenylethyl alcohol in a low cost process. This material is a valuable intermediate in the preparation of fragrances and of styrene, a commercial chemical with widely varying uses. In the past, it has been proposed that β-phenylethyl alcohol be prepared from benzyl alcohol. For example, the reaction has been described by Wender, I. et al., J. Am. Chem. Soc. 71 (1949), pages 4160–4161 in the presence of a cobalt catalyst. This early work is summarized by Orchin in Advances in Catalysis, Vol. V (1953), pages 393–414. This author reports that, at 185° C., a 50–60% yield of toluene and a 25–35% yield of β-phenylethanol is obtained. Other workers have experimented with this reaction, particularly Y. B. Kryukov et al., Neftekhimiya, 1970, 10 (1), at page 83. Here, a vapor phase reaction is described over an iron, alumina, vanadium and potassium catalyst at 450° C. and 50 atmospheres pressure. Unfortunately, in this latter reaction extremely low selectivities to the β-phenylethanol were obtained.

Though not related to the formation of β-phenylethanol, homologation has been described by a series of patents assigned to Commercial Solvents, including U.S. Pat. Nos. 3,248,432 and 3,285,948, British Pat. No. 951,506, and Belgian Pat. Nos. 618,413 and 625,939. These references are primarily concerned with the homologation of methanol to form ethanol. The catalyst system shown in the U.S. Pat. No. 3,285,948 is of particular interest. This patent discloses the use of a cobalt catalyst promoted with a ruthenium or osmium halide and iodine. The patent also discloses the optional use of from 0.1 to 20% of water based on the methanol charged in the reaction system. Reaction temperatures indicated are 175° to 230° C., preferably from 190° to 210° C.

Unfortunately, the foregoing references fail to result in the preparation of high yields of β-phenylethanol. The work reported by Orchin forms so little β-phenylethanol that such reaction could not be considered of commercial importance. On the other hand, the work by Commercial Solvents on methyl alcohol does not suggest the homologation of benzyl alcohol.

The process of the present invention, which is distinguishable from the foregoing prior art, surprisingly yields high selectivity to the desired β-phenylethanol. Selectivities of over 60% are obtained, in certain instances, up to 80%. This is over twice the selectivity to β-phenylethanol reported in the prior art. This surprising improvement results from performing the process in the presence of a promoted cobalt catalyst and at least some water at a temperature substantially lower than that taught in the prior art, namely, from 100° to 165° C. Further improvements are obtained by using selected hydrogen to carbon monoxide ratios and even more specific temperatures.

BRIEF SUMMARY OF INVENTION

The present invention relates to a process for producing β-phenylethyl alcohol from benzyl alcohol at high selectivity and yields. The process includes contacting a liquid feedstock containing benzyl alcohol with a gaseous mixture of hydrogen and carbon monoxide in the presence of a ruthenium and iodide promoted cobalt catalyst at a pressure of at least 70 atmospheres and performing the reaction in the presence of at least 0.1 weight percent of water (based on the feedstock) at a temperature of from 100° to 165° C. Further improvements are obtained by controlling the ratio of the hydrogen and the carbon monoxide.

DETAILED DESCRIPTION OF THE INVENTION

The present invention relates to a process for the production of β-phenylethyl alcohol and particularly to its production from benzyl alcohol in the presence of a promoted cobalt catalyst. β-Phenylethyl alcohol is a known article of commerce used for the preparation of organic chemicals in fragrance materials. It is also a valuable intermediate in the preparation of styrene.

In the present invention, it has surprisingly been discovered that the homologation of benzyl alcohol to β-phenylethyl alcohol may be greatly improved by performing the reaction in the presence of water at reaction temperatures of from 100° to 165° C., i.e., temperatures considerably lower than those taught in the prior art. By following the teachings of the present invention, selectivities in excess of 60% may be obtained. Minimum amounts of by-products such as toluene, benzyl ethers, and higher ethers and alcohols are formed. The reaction takes place in the presence of a cobalt catalyst promoted with ruthenium and iodide salts. It is preferred to use selected hydrogen-to-carbon monoxide ratios and pressure ranges to achieve even more outstanding results.

In performing the reaction, the benzyl alcohol, containing at least 0.1 weight percent of water, hydrogen and carbon monoxide are reacted at a temperature of from 100° to 165° C., preferably from 120° to 150° C. Up to 15 weight percent of water may be used, preferably 1 to 10%. In determining the amount of water to be used, it is desirable to avoid the formation of a separate water phase. The formation of a water phase is detrimental because the catalyst is water-soluble and will be extracted from the organic reaction phase into such water phase. Greater amounts of water may be used if a solvent which prevents the formation of a separate water phase is added to the reaction medium. Such coupling solvents include ethylene glycol, propylene glycol, diethylene glycol and dioxane, and are well known to those skilled in the art.

The feedstock to the reaction is preferably at least 50% benzyl alcohol. Other organic constituents may be present, so long as they do not interfere with the homologation.

The cobalt catalysts used in the present invention may be present from 0.25% to 5.0%, calculated as moles of cobalt catalyst (as Co) to moles of the benzyl alcohol multiplied by 100. Over this range, variations in the amount of catalyst are not particularly critical. As a practical matter, from 1.0 to 3.0 mole percent are employed. The cobalt catalyst added to the system is selected so as to be soluble in the reaction medium. The active form of the cobalt catalyst is believed to be cobalt tetracarbonyl hydride [$HCo(CO)_4$]. This cobalt carbonyl can be formed in situ by adding to the system a cobalt tetracarbonyl hydride-yielding compound, such as an organic salt of cobalt, particularly a water-soluble compound, e.g., cobalt acetate, cobalt formate, or cobalt propionate. Such materials are readily converted to the active cobalt from during the reaction.

The promoters employed, i.e., the ruthenium and the iodide salts, are used in combination. The ruthenium salt is most desirably added as the halide, and from 0.02 to 0.30 atoms of ruthenium should be present for each atom of cobalt, preferably from 0.04 to 0.15. In the case of the iodide salt, this may be formed by adding elemental iodine to the reaction system or by introducing a salt form of the iodide, such as an alkali metal iodide. Generally, from 0.05 to 2.0 atoms of iodide per atom of cobalt should be present, preferably from 0.10 to 1.0.

Such promoted catalysts may be prepared in accordance with the teaching of U.S. Pat. No. 3,285,948, assigned to Commercial Solvents.

The amount of hydrogen and carbon monoxide added is generally in stoichiometric excess of the amount of benzyl alcohol used. As a minimum, at least stoichiometric quantities must be added and excesses up to 10 times the stoichiometric amount are useful.

The advantages of the present invention may be obtained over a wide range of hydrogen to carbon monoxide ratios. As little as one-half mole of hydrogen to each mole of carbon monoxide may be used, and up to five moles of hydrogen to carbon monoxide may be used. The most preferred range is from 3:1 to 1:1. Sufficient carbon monoxide must be present to maintain the cobalt catalyst in its active state.

The reaction pressure should be from at least 70 to 400 atmospheres, most preferably from 200 to 300 atmospheres. Increased pressures tend to favor selectivity to the $\beta$-phenylethyl alcohol. However, the use of higher ranges of pressure is limited by practical considerations such as the selection of equipment and safety factors.

The reaction period is not critical, but should be selected so as to achieve acceptable conversions without unduly lengthening the process cycles. As a practical matter, the reaction period would range from one-half to three hours.

The following examples further illustrate the present invention.

EXAMPLE 1

The reactor used for these tests is a 400 cc. high pressure Parr autoclave made of Hastelloy C. It has a detachable head, a magnetic bar stirrer, an external electric jacket heater, and an internal coil cooler through which air is passed. Synthesis gas was provided by premixed cylinders and was raised to reaction pressure by use of a booster compressor. The gas flow is normally maintained at from 1 to 4.1./min. (measured at 20° C. and one atm. pressure).

The runs were performed as follows: The disassembled autoclave was charged with benzyl alcohol, catalyst and the stirring bar and sealed. The unit was sparged and pressurized to 35 atm. with nitrogen. The stirrer and the heaters were then started, bringing the reaction to the desired temperature. At this point, synthesis gas was added, bringing the reactor to 80 atm. pressure. The selected pressure was maintained by use of a diaphragm-type back pressure regulator. Effluent gases from the autoclave were passed through a condenser to remove liquid from the gas stream and the liquid was recycled to the autoclave. After the reaction conditions were maintained for the desired run time, the autoclave was cooled, sparged with nitrogen, and depressurized. The reaction contents were then analyzed by gas-liquid chromatography.

Table A describes the specific runs and the results obtained. The feed gas contained equal moles of hydrogen and carbon monoxide and was passed to the system at 270 atm. pressure for a period of four hours. The liquid feed was composed of 4.0 weight percent cobalt as cobalt carbonyl [$Co_2(CO)_8$] based on benzyl alcohol (2.6 mole % Co based on benzyl alcohol) and 0.25 atom of iodide as sodium iodide (NaI) per atom of cobalt and 0.105 atom of ruthenium as ruthenium chloride ($RuCl_3$) per atom of cobalt and about 200 grams of benzyl alcohol. Water was added to the liquid feed where indicated. In addition to $\beta$-phenylethanol and toluene, the reaction produces a certain amount of ethers and higher alcohols.

Table A

| Run No. | Temp. °C. | Feed Water Content Wt. % | Benzyl Alcohol Conversion | Molar Selectivity to | |
|---|---|---|---|---|---|
| | | | | $\beta$-Phenyl-ethanol | Toluene |
| 1 | 180 | 0 | 68.3 | 10.8 | 78.1 |
| 2 | 180 | 7.3 | 76.9 | 23.6 | 69.1 |
| 3 | 130 | 0 | 43.5 | 35.4 | 48.4 |
| 4 | 140 | 7.3 | 46.6 | 62.2 | 23.9 |
| 5 | 130 | 7.3 | 39.5 | 73.1 | 16.7 |
| 6 | 120 | 7.3 | 21.2 | 80.0 | 10.5 |

Runs 1 and 2 reproduce the temperature conditions described by Orchin and by the aforementioned Commercial Solvents patents. In Run 2 water is present. Run 3 shows low temperature operation without water addition. Runs 4, 5 and 6 illustrate the practice of the subject invention, using water addition and the preferred temperature range. Run 5, by comparison with Run 3, shows that if there is no water in the feed, even at the desired temperature range, a substantial loss of selectivity to $\beta$-phenylethanol occurs.

Examples 4, 5 and 6 show unexpectedly high molar selectivities to the $\beta$-phenylethanol. These are all between 60 and 80% and considerably in excess of the low amounts shown in Runs 1 to 3. The results obtained in Runs No. 1 and 2 compare with those reported in the prior art by Orchin.

EXAMPLE 2

A series of reactions at 130° C. was carried out in the same manner as described in Example 1. These are described in Table B. In all cases, 7.3 weight percent water was added to the feed, but the feed gas molar composition was varied from 1:2 to 2:1 hydrogen to carbon monoxide.

Table B

| Run No. | Feed Gas $H_2$:CO Molar Ratio | Benzyl Alcohol Conversion | Molar Selectivity to | |
|---|---|---|---|---|
| | | | $\beta$-Phenylethanol | Toluene |
| 1 | 1:2 | 34.0 | 70.2 | 19.6 |
| 2 | 1:1 | 39.5 | 73.1 | 16.7 |
| 3 | 2:1 | 47.1 | 78.5 | 15.9 |

This series of runs illustrates the advantageous effects of increased hydrogen to carbon monoxide ratios.

EXAMPLE 3

A series of reactions at 130° C. was carried out in the same manner as described in Example 1. In all cases, 7.3 wt. % water was added to the feed, but the quantities of catalyst promoters were varied.

Table C

| Run No. | Atoms NaI / Atom cobalt | Atoms RuCl₃ / Atom cobalt | Benzyl Alcohol Conversion | Molar selectivity to β-Phenyl-ethanol | Toluene |
|---|---|---|---|---|---|
| 1 | 0.25 | 0.10 | 39.5 | 73.1 | 16.7 |
| 2 | 0 | 0.10 | 43.6 | 27.6 | 23.5 |
| 3 | 0.25 | 0 | 68.0 | 17.0 | 38.1 |

The foregoing table shows that the presence of both the sodium iodide and the ruthenium chloride promoters are required to obtain high selectivity to β-phenylethanol.

We claim:

1. A process for the preparation of β-phenylethyl alcohol which comprises reacting a feedstock containing benzyl alcohol in the presence of at least 0.1 weight percent water (based on the feedstock) with a mixture of hydrogen and carbon monoxide in the presence of a cobalt catalyst promoted with a ruthenium and an iodide compound at a pressure of at least 70 atmospheres and at a temperature of from 100° to 165° C.

2. The process of claim 1 wherein the ratio of hydrogen to carbon monoxide is greater than 1:1.

3. The process of claim 1 wherein the temperature is from 120° to 150° C.

4. The process of claim 1 wherein a stoichiometric excess of hydrogen and carbon monoxide, based on benzyl alcohol, is added to the reaction.

5. The process of claim 1 wherein the cobalt catalyst is promoted with from 0.02 to 0.30 atom of ruthenium and from 0.50 to 2.0 atoms of iodine per atom of cobalt.

6. A process for preparing β-phenylethyl alcohol which comprises reacting a liquid feedstock containing at least 50% benzyl alcohol and from 1 to 10 weight percent water with a mixture of hydrogen and carbon monoxide in the presence of a cobalt catalyst promoted with ruthenium and iodide salts at a temperature of from 120° to 150° C., and at a pressure of from 200 to 300 atmospheres, thereby forming a reaction product containing β-phenylethyl alcohol.

* * * * *

UNITED STATES PATENT AND TRADEMARK OFFICE
CERTIFICATE OF CORRECTION

PATENT NO. : 4,158,100
DATED : June 12, 1979
INVENTOR(S) : Martin B. Sherwin & Arthur M. Brownstein It is certified that error appears in the above-identified patent and that said Letters Patent are hereby corrected as shown below:

Claim 5, line 3: cancel "0.50" and substitute --0.05-- therefor.

Signed and Sealed this

Twenty-fifth Day of September 1979

[SEAL]

Attest:

Attesting Officer

LUTRELLE F. PARKER
Acting Commissioner of Patents and Trademarks